(12) United States Patent
Reinstaedtler (10) Patent No.: US 11,635,425 B2
(45) Date of Patent: *Apr. 25, 2023

(54) BREATH GAS ANALYSIS SYSTEMS AND METHODS

(71) Applicant: VYAIRE MEDICAL GMBH, Höchberg (DE)

(72) Inventor: Juergen Reinstaedtler, Wuerzburg (DE)

(73) Assignee: VYAIRE MEDICAL GMBH, Höchberg (DE)

(*) Notice: Subject to any disclaimer, the term of this patent is extended or adjusted under 35 U.S.C. 154(b) by 227 days.

This patent is subject to a terminal disclaimer.

(21) Appl. No.: 17/100,320

(22) Filed: Nov. 20, 2020

(65) Prior Publication Data

US 2021/0072225 A1    Mar. 11, 2021

Related U.S. Application Data

(63) Continuation of application No. 16/682,997, filed on Nov. 13, 2019, now Pat. No. 10,883,979, which is a
(Continued)

(30) Foreign Application Priority Data

May 5, 2015    (DE) .................... 10 2015 106 949.0

(51) Int. Cl.
*G01N 33/497*    (2006.01)
*A61B 5/083*    (2006.01)
(Continued)

(52) U.S. Cl.
CPC ............. *G01N 33/497* (2013.01); *A61B 5/08* (2013.01); *A61B 5/083* (2013.01); *G01N 33/0006* (2013.01)

(58) Field of Classification Search
CPC .................... G01N 33/497; G01N 33/0006
(Continued)

(56) References Cited

U.S. PATENT DOCUMENTS 4,278,636 A    7/1981    Voigt et al.
10,527,606 B2    1/2020    Reinstaedtler
(Continued)

FOREIGN PATENT DOCUMENTS

EP    2034311    3/2009
FR    2709000    2/1995
WO    WO-2013121165    8/2013

OTHER PUBLICATIONS

European Office Action for Application No. 16721155.6, dated Sep. 24, 2018, 5 pages.
(Continued)

*Primary Examiner* — John Fitzgerald
*Assistant Examiner* — Rodney T Frank
(74) *Attorney, Agent, or Firm* — Morgan, Lewis & Bockius LLP (57) ABSTRACT

Devices and methods are provided for breath gas analysis when determining the difference in the concentrations of at least one gas in the exhaled breathing air on the one hand and in the ambient air on the other hand. The device may include at least one gas sensor, by means of which the concentration of a gas can be determined, and a line system, through whose lines the exhaled air to be examined, the ambient air and a calibrating gas can be selectively pumped to the gas sensor. The method may include feeding ambient air; feeding calibrating gas to the gas sensor; feeding exhaled air to the gas sensor; feeding calibrating gas to the gas sensor again; and feeding exhaled air to the gas sensor again.

20 Claims, 9 Drawing Sheets

Related U.S. Application Data continuation of application No. 15/143,350, filed on Apr. 29, 2016, now Pat. No. 10,527,606.

(51) Int. Cl.
  *A61B 5/08* (2006.01)
  *G01N 33/00* (2006.01)

(58) Field of Classification Search
  USPC ......................................................... 73/23.3
  See application file for complete search history.

(56) References Cited

U.S. PATENT DOCUMENTS

| | | | |
|---|---|---|---|
| 10,883,979 B2 * | 1/2021 | Reinstaedtler | ....... A61B 5/0836 |
| 2010/0002234 A1 | 1/2010 | Cormier | |
| 2011/0072883 A1 | 3/2011 | Abraham-Fuchs et al. | |

OTHER PUBLICATIONS

Extended European Search Report for Application No. 20172477.0, dated Oct. 5, 2020, 10 pages.

International Search Report and Written Opinion for Application No. PCT/EP2016/060056, dated Jul. 18, 2016, 12 pages.

* cited by examiner

BREATH GAS ANALYSIS SYSTEMS AND METHODS

CROSS-REFERENCE TO RELATED APPLICATIONS

This application is a continuation of U.S. application Ser. No. 16/682,997, entitled "BREATH GAS ANALYSIS SYSTEMS AND METHODS," filed on Nov. 13, 2019, which issued as U.S. Pat. No. 10,883,979 on Jan. 5, 2021, which is a continuation of U.S. application Ser. No. 15/143,350, entitled "BREATH GAS ANALYSIS SYSTEMS AND METHODS," filed Apr. 29, 2016, which issued as U.S. Pat. No. 10,527,606 on Jan. 7, 2020, which claims priority to German Application Serial No. DE102015106949.0, entitled "BREATH GAS ANALYSIS SYSTEMS AND METHODS," filed May 5, 2015, which are hereby incorporated by reference in their entirety for all purposes.

TECHNICAL FIELD

The present disclosure generally relates to breath gas analysis and, in particular, relates to systems and methods for calibrated breath gas analysis.

BACKGROUND

Devices for breath gas analysis for medical diagnostics or lifestyle applications have been used for a long time to be able to make statements regarding the lung function or other body functions of a subject. Methods of this kind are used in particular in the field of ergospirometry. The analysis of the breath gas can provide information on many metabolic processes of the human body.

SUMMARY

In some scenarios, prior to breath gas analysis using a semiconductor detector, prior to the actual measurement of the breath alcohol content, the semiconductor is calibrated in each case. Breath gas analysis devices are described, as examples, in DE 20 2009 018 824 U1 and DE 29 12 181 C2, which, for example, describe a breath alcohol measuring instrument having a semiconductor sensor, and both of which are hereby incorporated herein by reference in their entireties.

A calibrating gas may be used for the calibration, which consists of ambient air and a vapor of, for example, one percent alcohol. Once the actual measurement has been completed, the semiconductor sensor is purged with ambient air to remove all residue of alcohol vapor from the measuring assembly. It can be of great importance for the validity of the breath gas analysis that the gas sensors used for determining the concentration of a specific gas in the exhaled air are carefully calibrated. On the one hand, said calibration pertains in particular to zero-point comparison, by which the measuring signal of the gas sensor is calibrated to a specific reference value of the gas concentration to be determined. On the other hand, said calibration pertains to an amplification of the gas sensor so that a change in the gas concentration is translated into a proportional change in the measuring signal of the gas sensor. The present disclosure is concerned, in some aspects, with the zero-point comparison of the gas sensor in breath gas analyzing devices.

In some breath gas analyzing devices, the gas sensor is calibrated using ambient air and using calibrating gas prior to the beginning of the actual gas analysis on the subject. The ambient air is used to calibrate the gas sensor to a specific zero point because the concentration of certain gases in the ambient air is generally very stable and can be reliably predicted with sufficient certainty. Moreover, on average, the ambient air contains, for example, 20.9% oxygen and, for example, 0.05% CO2. When calibrating the gas sensor to zero, these gas concentrations of the ambient air may be taken as a basis. If the ambient air is now fed through the gas sensor, the measuring signal thus obtained is calibrated to the gas concentration to be expected in the ambient air. For example, the concentration of oxygen may be calibrated to 20.9%. In view of the calibration of the amplification of the gas sensor measuring signal, a breath gas analyzing device may use a calibrating gas, which is tapped from a gas cylinder, for example.

However, regarding zero-point calibration of the gas sensor, if care is not taken, there can be measurement errors due to gas sensors being prone to so-called zero-point fading (sometimes referred to as Nullwert-Fading). In other words, this means that the zero point of the gas sensor can change during a measurement because of the technical properties of the gas sensor. In some situations, severe measurement errors may occur if these changes in the zero point are not taken into account. Hence, breath gas analyzing devices may be provided that recalibrate the zero point at regular intervals also during a measurement.

In the course of this zero-point calibration, ambient air may be fed to the gas sensor instead of the exhaled air to be analyzed so as to recalibrate the gas sensor to the correspondingly known gas concentration value of the ambient air. A pneumatic switch valve may be used for switching from exhaled air to ambient air. It can be important for the accuracy of a breath gas analyzing device to observe the changes in gas concentration at the suction point as precisely as possible. In particular, at the beginning and at the end of the exhalation, these changes in gas concentration can occur very suddenly. Because of the gas path, there is the risk that the changes in gas concentration may weaken and thus become distorted. Complex gas paths with poorly purged volumes, as they are often found in pneumatic valves, pose an increased risk in this case.

Therefore, according to various embodiments, a method for operating a new device is provided for breath gas analysis when determining the difference in the concentrations of at least one gas in the exhaled breathing air and in the ambient air, by means of which the complexity of the device and the potential distortion of the changes in gas concentration due to the pneumatic valve system during the actual breath gas analysis can be reduced.

One or more embodiments include a method of breath gas analysis, determining, by at least one gas sensor of a device for breath gas analysis, a first gas concentration in ambient air received from a first intake of the device through a first line path between the first intake and the at least one gas sensor, determining an ambient air reference value based on the first gas concentration, determining, by the at least one gas sensor, a second gas concentration in a calibrating gas received from a second intake of the device through a second line path between the second intake and the first line path, the second line path comprising a valve configured to selectively provide the calibration gas to displace ambient air along the first line path, determining a calibrating gas reference value based on the second gas concentration, determining, by the at least one gas sensor, a third gas concentration in exhaled air received through the first line path from the first intake, determining a measured value based on the third gas concentration, determining, by the at least one gas sensor, a fourth gas concentration in additional calibrating gas received through the second line path from the second intake, determining a correction value based on a difference between the fourth gas concentration and the calibration gas reference value, determining a corrected ambient air reference value based on the correction value, determining, by the at least one gas sensor, a fifth gas concentration in additional exhaled air received through the first line path from the first intake, and performing a breath gas analysis of the fifth gas concentration using the corrected ambient air reference value.

One or more embodiments include a device for performing the method of breath gas analysis. The device includes the first intake disposed external to the device; the first line path extending from the first intake into the device; the at least one gas sensor disposed within the device along the first line path; the second intake disposed external to the device; the second line path extending from the second intake into a first portion of the device; the valve disposed within the device along the second line path; and the second line path extending out of a second portion of the device and terminating into the first line path external to the device.

One or more embodiments include a device for performing the method of breath gas analysis. The device includes the first intake disposed external to the device; the first line path extending from the first intake into the device; the at least one gas sensor disposed within the device along the first line path; the second intake disposed external to the device; the second line path extending from the second intake into the device and terminating into the first line path within the device; and the valve disposed within the device along the second line path.

According to another embodiment, a method is provided that includes: providing ambient air along a line path of a gas analysis device to a gas sensor disposed within the device; providing exhaled air from a subject along the same line path to the gas sensor; and providing a calibration gas along the same line path to the gas sensor while the line path is open to the ambient air or the exhaled air.

In in a first step of a method according to an embodiment, ambient air is fed to the gas sensor to determine the gas concentration in the ambient air. The output signal of the gas sensor thus obtained is associated with the gas concentration known per se of the corresponding gas in the ambient air, such as 20.9% oxygen, and is temporarily stored as an ambient air reference value.

Subsequently, according to various embodiments, a calibrating gas is fed to the sensor, said calibrating gas also containing a gas of the corresponding sort, such as oxygen. The gas concentration of this gas in the calibrating gas is determined by the gas sensor, too, and the corresponding output signal of the gas sensor is temporarily stored as a calibrating gas reference value.

In the next step, according to various embodiments, the actual breath gas analysis begins. To this end, the subject is connected to the line system of the device, for example by means of a correspondingly suitable mouthpiece, and the exhaled air of the subject is fed to the gas sensor. Using the reference values stored in the device, in particular using the ambient air reference value determined in operation (a) noted above, the difference in the gas concentrations in the exhaled air on the one hand and in the ambient air on the other hand is determined.

At some point a shift of the measurement characteristic of the gas sensor may occur, such as after a certain measuring time has elapsed. Thus, according to various embodiments, no ambient air is fed to the gas sensor to recalibrate the gas sensor. Instead, the calibrating gas previously used in operation (b) above is fed to the gas sensor again and the gas concentration of the corresponding gas in the calibrating gas is determined. The output signal of the gas sensor thus obtained is subsequently compared to the calibrating gas reference value previously determined in operation (b), for example. The difference thus obtained between the measuring signals may be regarded as the degree of the change in the measurement characteristic of the gas sensor. If the difference is close to zero, the measured-value characteristic of the gas sensor has not changed. The measured-value difference obtained in this step is stored in the evaluating device as a correction value.

Subsequently, according to various embodiments, the actual breath gas analysis is continued and exhaled air is fed to the gas sensor again for this purpose. The output signal of the gas sensor thus obtained is temporarily stored as a measured value and is evaluated in the evaluating device to determine the gas concentration in the exhaled air. The evaluation takes place using the ambient air reference value and the correction value. Thus, in various embodiments, the zero-point calibration may be repeatedly performed at certain intervals during the actual breath gas analysis, and may be performed not using ambient air, but using calibrating gas. In this way, a more accurate calibration may be performed, because a change in the measurement characteristic of the gas sensor is significantly characterized by the difference thus obtained between the calibrating gas reference value and the measuring signal of the gas sensor determined later by feeding of the calibrating gas. When the breath gas analysis is evaluated later, the correcting value thus obtained can be used to correct the ambient air reference value so as to avoid measurement errors that are caused by the change in the measurement characteristic of the gas sensor. For example, if a correcting value of 10% is obtained, this means that the gas sensor measures the gas composition of the calibrating gas with a measured-value characteristic that is changed by 10%. This change can then be proportionally applied to the ambient air reference value. By using the calibrating gas instead of the ambient air during zero-point recalibration, the complexity of the device can be reduced because the previously known valve systems for feeding the ambient air to the gas sensor are unnecessary during the actual breath gas analysis. At the same time, this omission of the valve system reduces the risk of distortion of the quick changes in gas concentration.

The measurement characteristic of gas sensors in breath gas analyzing devices can be highly sensitive to different pressure drops and/or changes of the gas flow velocity in the line paths used, via which the gas to be analyzed is fed to the gas sensor. If the calibrating gas and the exhaled air are fed to the gas sensor along different line paths, the resulting pressure-drop difference and/or changes of the gas flow velocity can cause a definitely relevant measurement error.

To preclude said measurement error in a simple manner, it is provided according to the present disclosure that the calibrating gas is fed to the gas sensor along the same common line path within the device as the exhaled air and the ambient air when determining the calibrating gas reference value and when determining the correction value later. As a result, it is achieved that there is the same pressure drop and the same gas flow velocity in each line path used during all gas analyses, namely during analysis of the gas concentration in the exhaled air, in the ambient air and in the calibrating gas, and differences and the resulting measurement errors are correspondingly avoided.

If calibrating gas is pumped to the gas sensor during the actual breath gas analysis to recalibrate the zero point of the gas sensor, the system may be operated to ensure that, prior to the actual determination of the correction value, the exhaled air is substantially completely displaced from the area of the gas sensor and from the upstream line paths. To realize this displacement in a simple manner, the calibrating gas can be pumped with a pumping capacity that is higher than the pumping capacity for pumping the breathing or ambient air through the device. The difference in pumping capacity with a higher pumping capacity for feeding the calibrating gas allows the calibrating gas to displace the exhaled air or the ambient air from the line paths toward the gas sensor and thus from the gas sensor itself without any other technical measures and while the line path remains open to the breathing air source or to the ambient air source. This is because, based on the higher pumping capacity, the corresponding line paths and thus the gas sensor are purged with the calibrating gas and there is no longer a way for the exhaled air or ambient air to reach the gas sensor despite the open line path.

In view of a simplified technical structure of the breath gas analyzing device, it may be desirable for the calibrating gas to be pumped from a pressurized gas cylinder into the line path toward the gas sensor. Thus, based on the pressure of the calibrating gas in the gas cylinder, a separate pumping device such as a feed pump for pumping the calibrating gas may be omitted in some embodiments.

If the calibrating gas is pumped through the device from a gas cylinder by means of pressure, the calibrating gas can preferably flow through at least one pressure throttle so as to correspondingly stabilize the pressure of the calibrating gas. However, a feed pump may be provided for pumping the exhaled air or the ambient air through the breath gas analyzing device.

To avoid variations of the changes in gas concentration, the feed pump may be connected downstream of the gas sensor so that the exhaled air or the ambient air is sucked through the gas sensor by the feed pump.

According to some embodiments, described is a valve that may be opened between the calibrating gas source, such as a pressurized gas cylinder, and the common line path when the calibrating gas is fed into the common line path. Because of the pressure in the calibrating gas source, the calibrating gas flows into the common line path when the valve is opened. At the same time, the line path toward the breathing air source or toward the ambient air source stays open as well, making the use of additional check valves expendable. The pumping capacity caused by the pressure of the calibrating gas in the common line path is higher than the pumping capacity caused by the feed pump so that the calibrating gas displaces the exhaled air or the ambient air from the common line path in the shortest time because of the difference in pumping capacity.

The feeding capacities at which the calibrating gas on the one hand and the exhaled air or the ambient air on the other hand are fed through the device are generally optional. A pumping capacity of 310 mL/min for the calibrating gas and of about 210 mL/min for the exhaled air or ambient air has proved especially suitable. The difference in pumping capacity of about 100 mL/min realizes an effective and resource-saving displacement of the exhaled air or ambient air by the calibrating gas.

To avoid the introduction of liquid droplets into the gas sensor, a purging vessel may be provided along the common line path in which liquid droplets are gravimetrically removed from the analyzed air stream.

Which gas concentrations are determined by the method according to the invention is also optional in general. The determination of the concentration of oxygen and the determination of the concentration of carbon dioxide are described herein as examples.

In summary, it is to be noted that the individual method steps of the measuring method according to the disclosure can of course be supplemented by additional intermediate steps. The individual method steps of the method according to the invention do not necessarily have to be performed successively without any intermediate steps. Instead, it is characteristic for the method according to the disclosure that the individual steps of the method according to the invention are performed without relying on the performance of additional intermediate steps between the individual stages of the method.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

Figure 1:
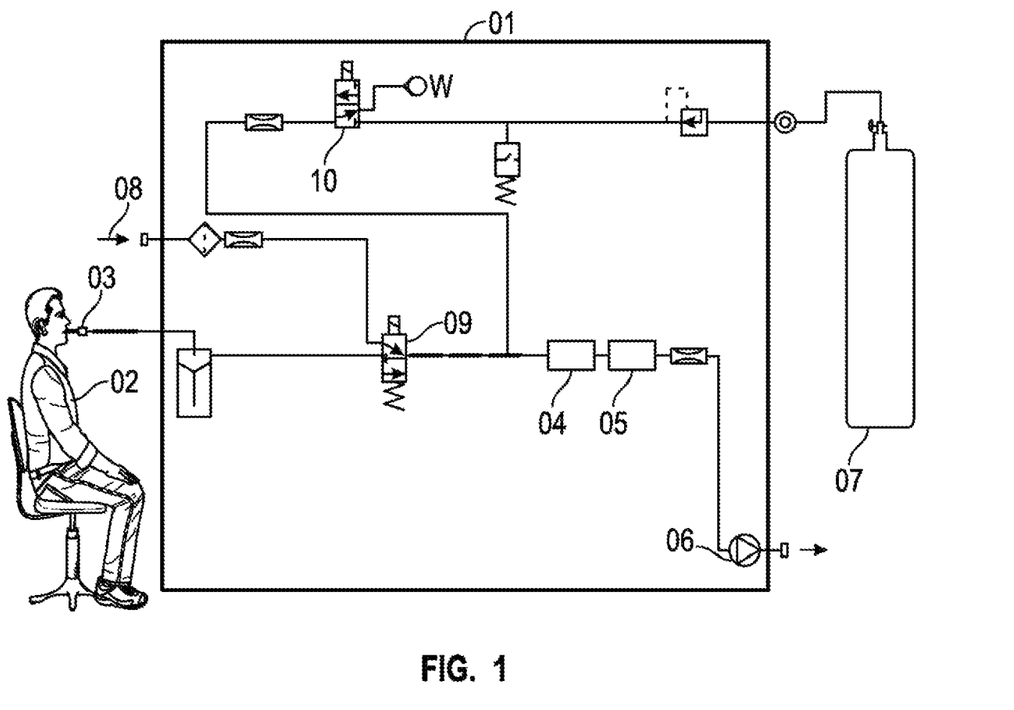
FIG. 1 is a diagram of a breath gas analyzing device during breath gas analysis in a schematic view according to certain aspects of the present disclosure.

FIG. 1 shows a device 01 for breath gas analysis, by means of which the gas concentration of oxygen and carbon dioxide in the exhaled breathing air of a subject can be measured, for example. In the example of FIG. 1, the subject 02 is connected to the line system of the device 01 by means of a suitable patient connection means, such as a mouthpiece 03 or a mask (with and without check valves) or a tube system, and the exhaled air is fed to the gas sensors 04 and 05 via the line system. By evaluating the measuring signals of the gas sensor 04, the carbon dioxide content can be determined, and by evaluating the measuring signals of the gas sensor 05, the oxygen content in the exhaled air can be determined. The exhaled air is pumped through the line system of the device 01 by means of a feed pump 06.

To calibrate the gas sensors 04 and 05 to a known reference value (zero point) at the beginning of the actual breath gas analysis, ambient air is suctioned from the surroundings via the empty mouthpiece 03 and fed to the gas sensors 04 and 05 before the subject 02 is connected to the device. The measuring signal of the CO2 gas sensor 04 thus obtained is calibrated to the ambient air reference value of 0.05% CO2 in the ambient air. The 02 gas sensor 05 is calibrated to the ambient air reference value of 20.9% oxygen.

To calibrate the measured-value amplification of the two gas sensors 04 and 05, a calibrating gas is subsequently fed from a gas cylinder 07 through the line system of the device 01 to the gas sensors 04 and 05 by switching the valve 10, and a corresponding amplification calibration is performed.

Since the measurement characteristic of the gas sensors 04 and 05 often changes in an undesired manner during the actual breath gas analysis because of so-called zero-point fading, it is provided with the device 01 that ambient air may again be fed to the gas sensors 04 and 05 at certain intervals for the purpose of zero-point calibration. To this end, the ambient air 08 can be suctioned in via another line path by switching the valve 09 and can be fed to the gas sensors 04 and 05 while the subject 02 is connected to the device 01. However, in the example of FIG. 1, the ambient air 08 will reach the gas sensors 04 and 05 along another line path than the breathing air during the actual breath gas analysis, which may lead to measurement errors. Moreover, the additional zero-point calibration during the actual breath gas analysis may be disadvantageous because the breath gas analysis is thus prolonged in an undesired manner.

Figure 2:
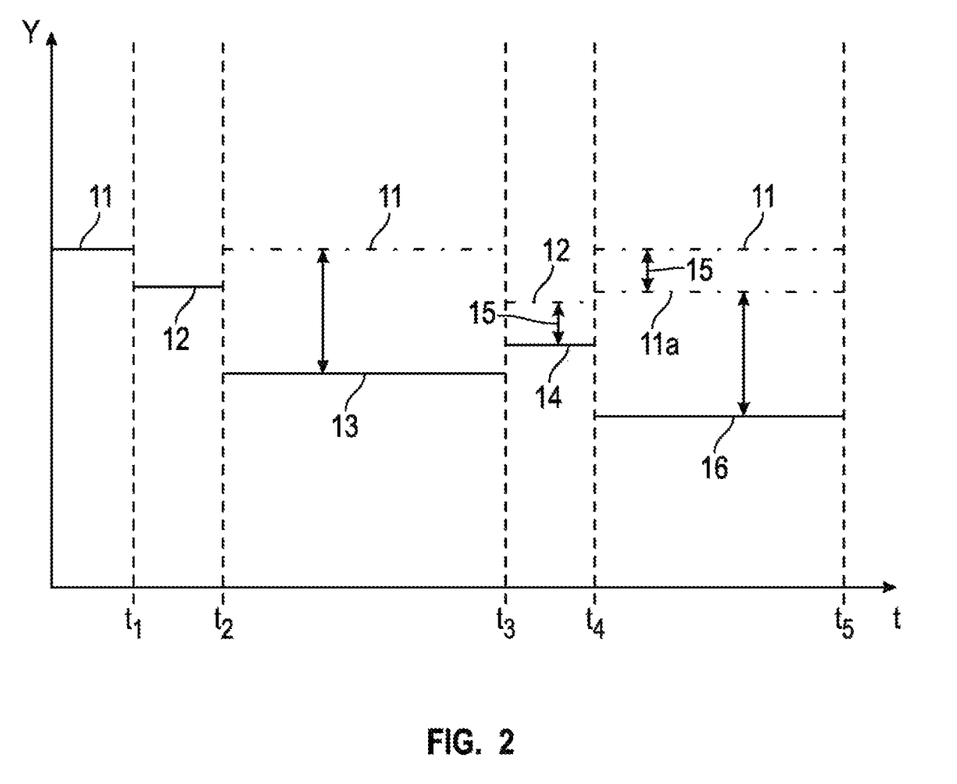
FIG. 2 illustrates a schematic illustration of a measurement diagram during determination of gas concentrations for breath gas analysis according to certain aspects of the present disclosure.
Figure 3:
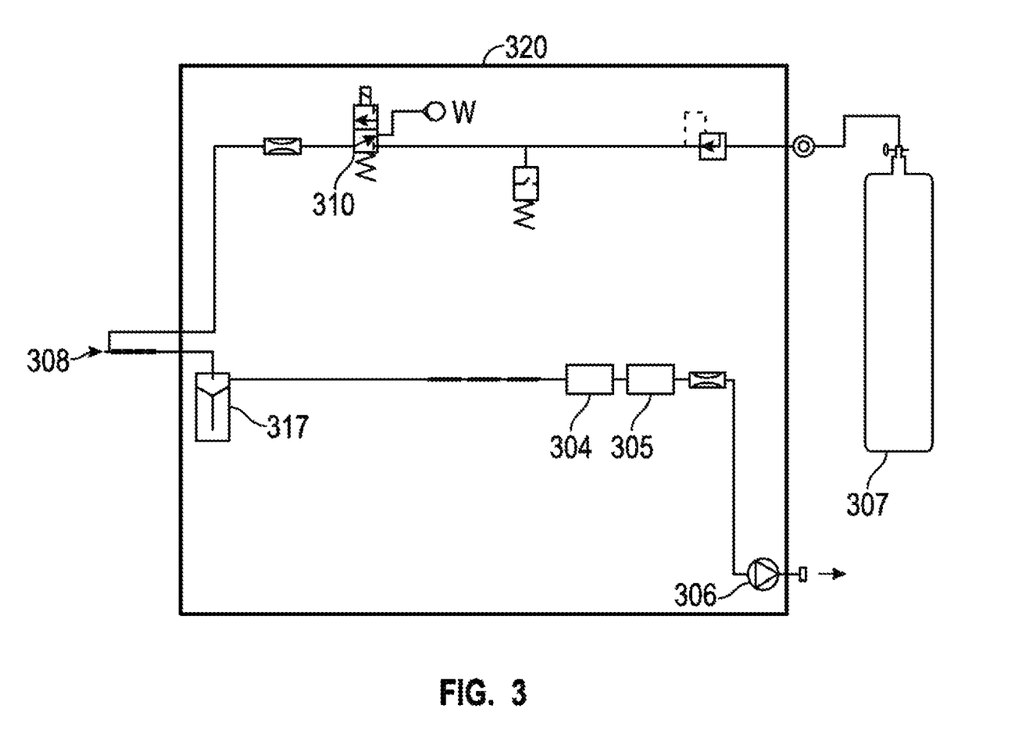
FIG. 3 illustrates a schematic diagram of a breath gas analyzing device during a first operation of a breath gas analysis according to certain aspects of the present disclosure.

FIG. 2 shows a schematically illustrated measurement diagram of a system for performing the methods according to the invention using a breath gas analyzing device 320 as shown in FIG. 3. As an example, the measuring signal Y of the gas sensor 305 for determining the oxygen concentration is marked over time. The illustration is schematic and serves to exemplify the systems, methods, and devices according to the present disclosure.

During a first operation, in the time between t0 and t1, the subject is not yet connected to the device 320 and ambient air 308 is pumped to the gas sensors 304 and 305 (e.g., an oxygen sensor and a carbon dioxide sensor) by, for example, being driven by the feed pump 306. The measuring signal 11 thus obtained, which with regard to oxygen, may (for example) correspond to a gas concentration of 20.9% oxygen, is stored as an ambient air reference value.

Figure 4:
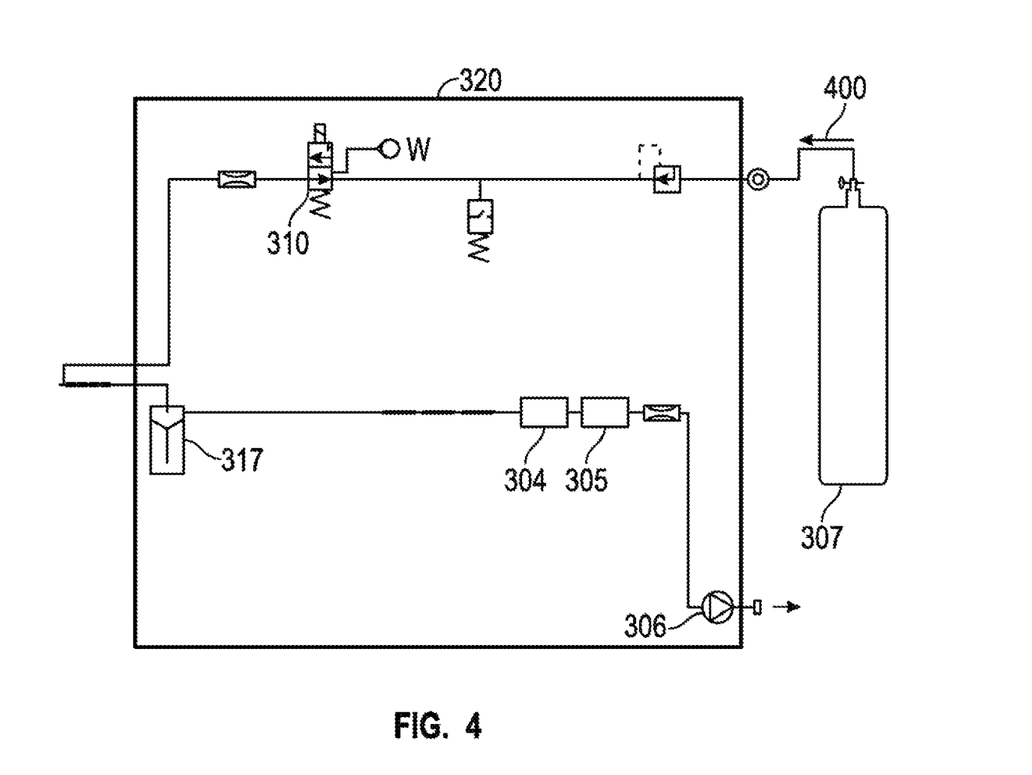
FIG. 4 illustrates a schematic diagram of the breath gas analyzing device of FIG. 3 during a subsequent operation of the breath gas analysis according to certain aspects of the present disclosure.

As schematically illustrated in FIG. 4, calibrating gas may be fed from the gas cylinder 307 (as indicated by arrow 400) through the line system of the device 320 to the gas sensors 304 and 305 by, for example, switching the valve 310. The calibrating gas may flow in at a pumping capacity of 310 mL/min, thus displacing the ambient air that is located in the line system and is fed at lower pumping capacity (e.g., a pumping capacity of only 210 mL/min) by the feed pump 306. Once the ambient air is completely displaced, the measuring signal 12, which (for example) corresponds to the oxygen concentration in the calibrating gas, is subsequently temporarily stored as a calibrating gas reference value in the time between t1 and t2 (FIG. 2).

Figure 5:
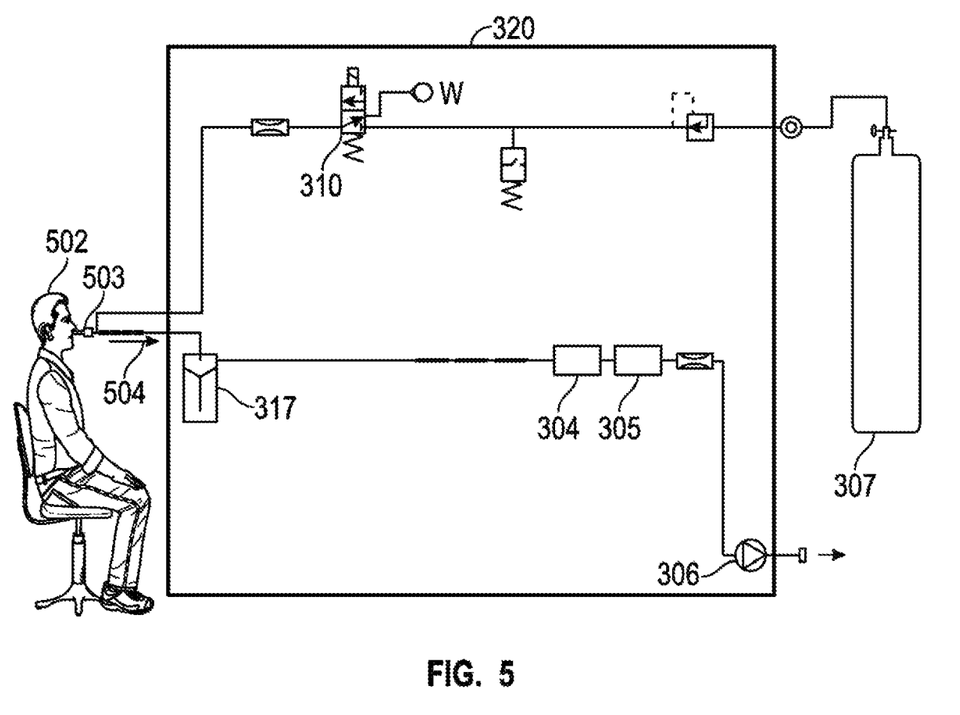
FIG. 5 illustrates a schematic diagram of the breath gas analyzing device of FIG. 3 during another subsequent operation of the breath gas analysis according to certain aspects of the present disclosure.

In a subsequent operation, as illustrated in the configuration of device 320 in FIG. 5, the subject 502 is connected to the device 503 (e.g., a mouthpiece attached to the intake) and the valve 310 is closed. In this way, the breathing air exhaled by the subject 502 (e.g., in the direction of arrow 504) now flows through the line system to the gas sensors 304 and 305. The gas concentration of oxygen can be exactly determined by evaluating the measuring signal 13 (FIG. 2) relative to the previously determined ambient air reference value. As shown in FIGS. 3-5, the ambient air and the exhaled air may flow from a first intake external to the device 320 along a first line path to the gas sensors 304 and/or 305 disposed within the device. The first line path may extend from the first intake external to the device to the gas sensor. The calibrating gas may flow along a second line path from a second intake external to the device for the calibrating gas. The second line path may extend from the second intake to a portion of the first line path that is disposed, for example, external to the device. The second line path may fluidly couple to the first line path at a location adjacent to the first intake (e.g., external to the device) so that calibration (calibration) gas is provided to the gas sensors along the same first line path as the ambient air and the exhaled air. Although the first and second line paths are shown converging at a location outside the device, this is merely illustrative. In other embodiments, the first and second line paths may converge at a location interior to the device and adjacent to the intake for exhaled and ambient air such that the calibration gas is provided to the gas sensor(s) along the same first line path as the ambient and/or exhaled air.

Valve 310 may be disposed on the second line path between the second intake and the portion of the first line path. Feed pump 306 may be disposed downstream of the gas sensors. Optional purge device 317 may be disposed on the first line path between the first intake and the gas sensors.

Figure 6:
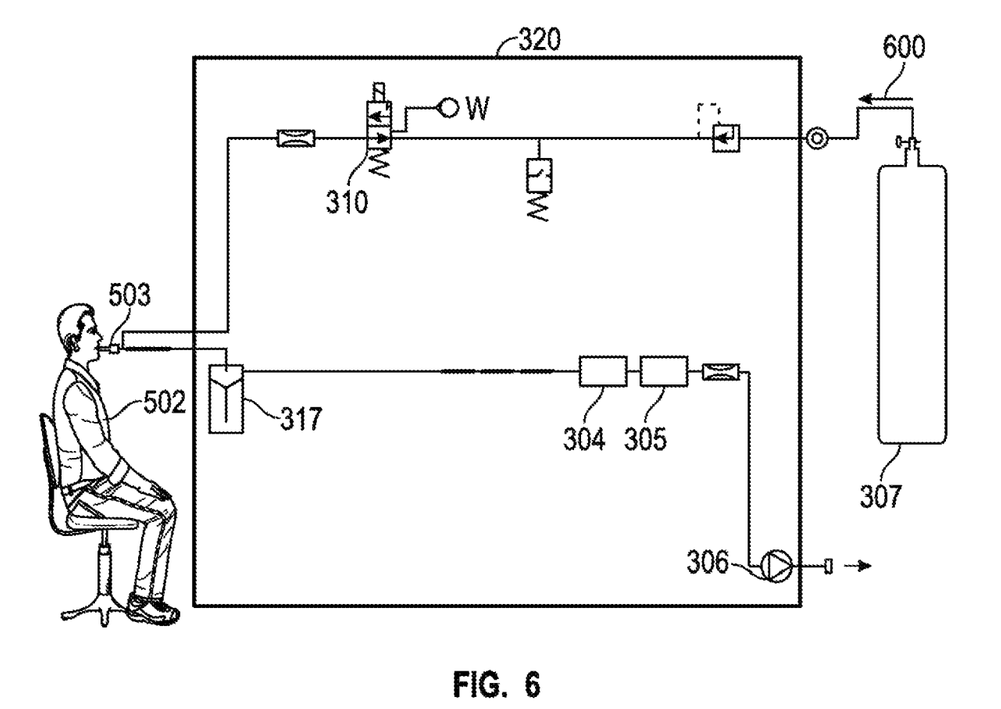
FIG. 6 illustrates a schematic diagram of the breath gas analyzing device of FIG. 3 during another subsequent operation of the breath gas analysis according to certain aspects of the present disclosure.

After a certain measuring period, a zero-point recalibration may be performed to be able to correct measurement errors by way of a changed measurement characteristic of the gas sensors 304 and 305. The subject 502 stays connected to the device 320 in the meantime. However, as indicated in FIG. 6, the valve 310 is opened and the calibrating gas flows from the gas cylinder 307 (as indicated by arrow 600) through the line system at a pumping capacity of, for example, 310 mL/min and displaces the exhaled air. Once the exhaled air has been substantially completely displaced, the gas concentration of, for example, oxygen in the reference gas is measured again in the time period between t3 and t4 (FIG. 2). The measuring signal 14 thus obtained is compared to the calibrating gas reference value and the difference 15 is stored in the evaluating device. The difference value 15 represents a degree of the change in the measurement characteristic of the gas sensor 305 and can be used to correct errors when evaluating the subsequent measurements.

Figure 7:
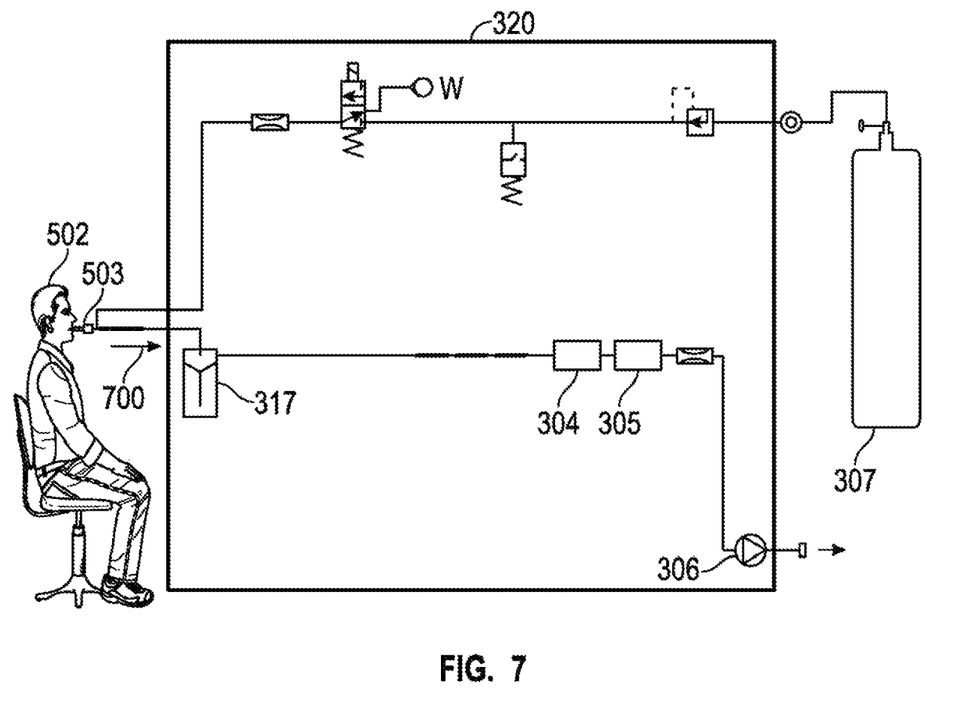
FIG. 7 illustrates a schematic diagram of the breath gas analyzing device of FIG. 3 during another subsequent operation of the breath gas analysis according to certain aspects of the present disclosure.

Finally, as illustrated in the configuration shown in FIG. 7, the exhaled air of the subject 502 may again be fed (e.g., in the direction of arrow 700) to the gas sensors 304 and 305 by closing the valve 310 and by operating the feed pump 306. When evaluating the resulting measuring signal 16 (FIG. 2) of the gas sensor 305, the correction value 15 is then taken into account as an additional value (e.g., to determine a corrected ambient air value 11a to which the measuring value 13 can be compared). The type of correction method to be selected for this purpose is to be selected according to the analyzing characteristic. The offset adjustment illustrated in FIG. 2 is to be understood as an example and does not limit the disclosure in its core.

An optional purging vessel 317 may be provided that serves to remove liquid droplets in the exhaled air. Additional method steps or operations may take place between the individual method steps described above. These steps, such as steps for displacing the gases following one another, are not illustrated in FIG. 2.

Figure 8A:
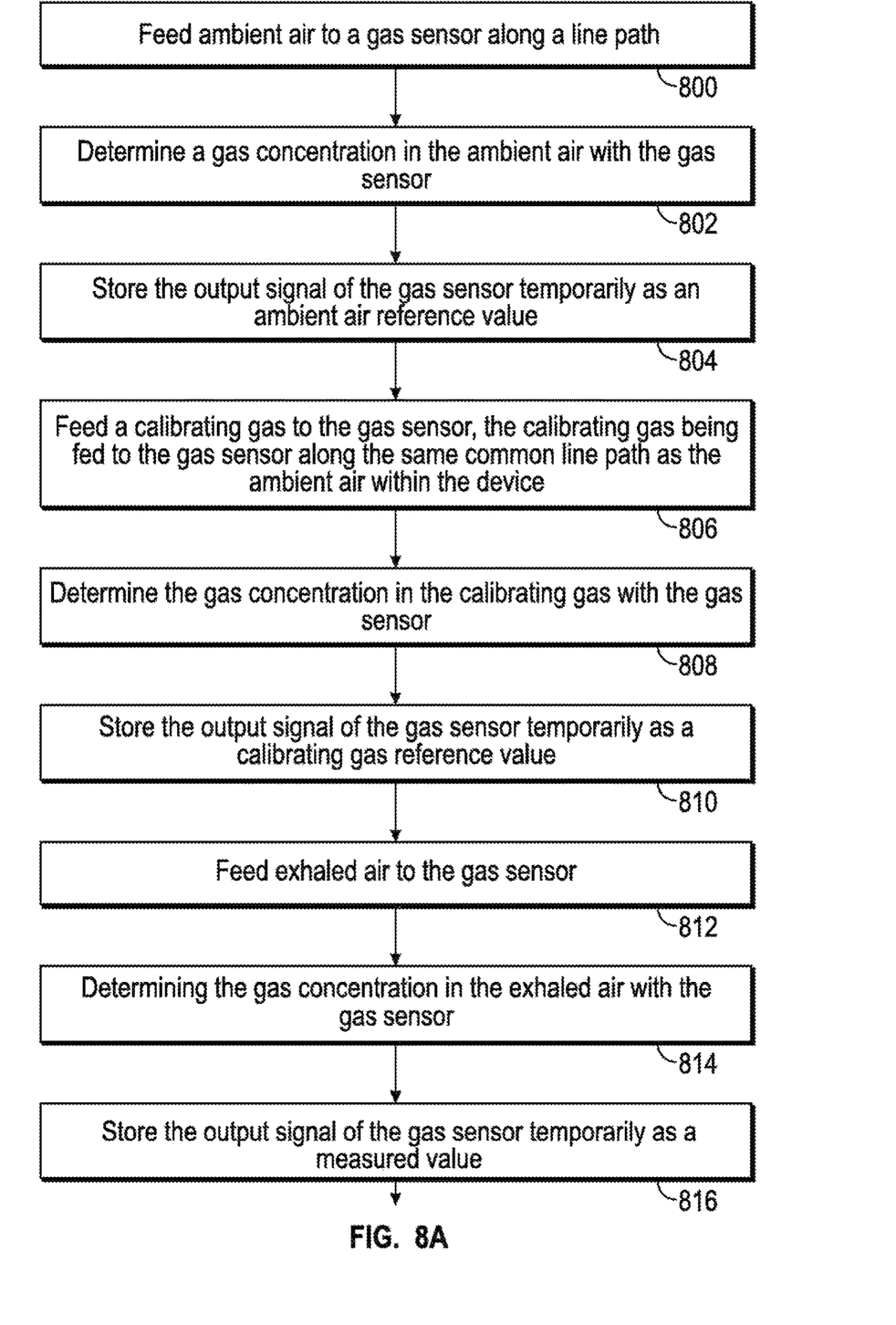
FIGS. 8A and 8B illustrate a flow chart of operations that may be performed for breath gas analysis according to certain aspects of the present disclosure.
Figure 8B:
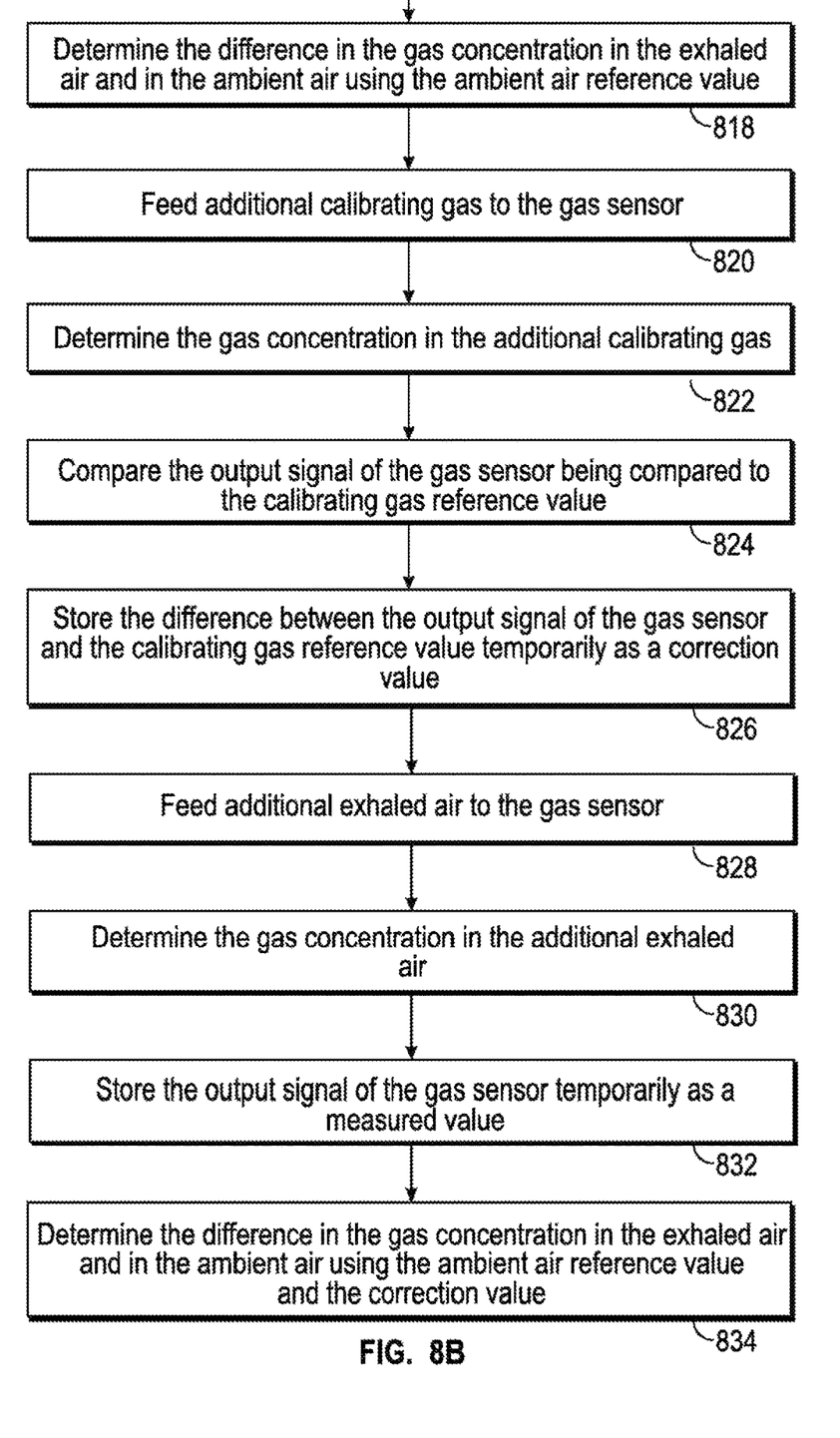

Illustrative operations that may be performed for calibrated breath gas analysis using, for example, the system of FIGS. 2-7, are shown in FIGS. 8A and 8B, according to an embodiment.

At block 800, ambient air may be fed to a gas sensor along a line path.

At block 802, a gas concentration in the ambient air may be determined with the gas sensor.

At block 804, the output signal of the gas sensor (e.g., a measurement value of the determined gas concentration in the ambient air) may be stored, at least temporarily, as an ambient air reference value.

At block 806, a calibrating gas may be fed to the gas sensor. The calibrating gas may be fed to the gas sensor along the same common line path as the ambient air within the device.

At block 808, the gas concentration in the calibrating gas may be determined with the gas sensor.

At block 810, the output signal of the gas sensor (e.g., a measurement value of the determined gas concentration in the calibrating gas) may be stored, at least temporarily, as a calibrating gas reference value.

At block 812, exhaled air (e.g., from a subject) may be fed to the gas sensor along the same line path.

At block 814, the gas concentration in the exhaled air may be determined with the gas sensor.

At block 816, the output signal of the gas sensor (e.g., a measurement value of the determined gas concentration in the exhaled air) may be stored, at least temporarily, as a measured value.

At block 818, the difference in the gas concentration in the exhaled air and the gas concentration in the ambient air may be determined using the ambient air reference value.

At block 820, additional calibrating gas may be fed to the gas sensor. The additional calibrating gas may be fed to the gas sensor along the same common line path as the ambient air within the device. The calibrating gas may be provided to the same common line path from an additional, second line path extending from an intake for the calibration gas to the first line path. Providing the calibrating gas and/or the additional calibrating gas may include operating a valve on the second line path to allow the calibrating gas to flow to the first line path.

At block 822, the gas concentration in the additional calibrating gas may be determined with the gas sensor.

At block 824, the output signal of the gas sensor (e.g., the gas concentration in the additional calibrating gas) may be compared to the calibrating gas reference value.

At block 826, the difference between the output signal of the gas sensor (e.g., the gas concentration in the additional calibrating gas) and the calibrating gas reference value may be stored, at least temporarily, as a correction value.

At block 828, additional exhaled air may be fed (e.g., from the same subject) to the gas sensor along the line path.

At block 830, the gas concentration in the additional exhaled air may be determined with the gas sensor.

At block 832, the output signal of the gas sensor (e.g., the gas concentration in the additional exhaled air) may be stored, at least temporarily, as a measured value (e.g., an additional measured value for the additional exhaled air).

At block 834, the difference in the gas concentration in the exhaled air (and/or the additional exhaled air) and in the ambient air may be determined using the ambient air reference value and the correction value.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A method, comprising:
feeding ambient air to a gas sensor along a line path of a gas analysis device;
determining a first gas concentration in the ambient air with the gas sensor;
storing a first output signal of the gas sensor temporarily as an ambient air reference value;
feeding calibrating gas to the gas sensor, the calibrating gas being fed to the gas sensor along the same common line path as the ambient air;
determining a second gas concentration in the calibrating gas with the gas sensor; storing a second output signal of the gas sensor temporarily as a calibrating gas reference value;
feeding exhaled air to the gas sensor along the same common line path;
determining a third gas concentration in the exhaled air with the gas sensor;
storing a third output signal of the gas sensor temporarily as a measured value; determining a difference between the third gas concentration in the exhaled air and the first gas concentration in the ambient air using the ambient air reference value;
feeding additional calibrating gas to the gas sensor along the same common line path;

determining a fourth gas concentration in the additional calibrating gas;
storing a fourth output signal of the gas sensor corresponding to the fourth gas concentration;
comparing the fourth output signal to the calibrating gas reference value;
storing a difference between the fourth output signal and the calibration gas reference value temporarily as a correction value;
feeding additional exhaled air to the gas sensor along the same common line path;
determining a fifth gas concentration in the additional exhaled air with the gas sensor;
storing a fifth output signal of the gas sensor temporarily as an additional measured value; and
determining a second difference between the fifth gas concentration in the additional exhaled air and the first gas concentration in the ambient air using the ambient air reference value and the correction value.

Concept 2. The method according to Concept 1 or any other Concept, wherein, while the calibrating gas is fed into the common line path, said common line path stays open toward a breathing air source of the exhaled air and/or an ambient air source, the calibrating gas being pumped into the common line path at a higher pumping capacity than the exhaled air and/or the ambient air, and the exhaled air and/or the ambient air being displaced from the common line path by the calibrating gas because of the difference in pumping capacity.

Concept 3. The method according to Concept 1 or any other Concept, wherein the calibrating gas is pumped into the common line path from a pressurized gas cylinder.

Concept 4. The method according to Concept 3 or any other Concept, wherein the calibrating gas flows through at least one pressure throttle.

Concept 5. The method according to Concept 1 or any other Concept, wherein the exhaled air and the ambient air are pumped into the common line path by being driven by a feed pump.

Concept 6. The method according to Concept 5 or any other Concept, wherein the exhaled air and the ambient air are pumped through the common line path by a vacuum generated by the feed pump downstream of the gas sensor.

Concept 7. The method according to Concept 5 or any other Concept, wherein, when the calibrating gas is fed into the common line path, a valve between a source of the calibrating gas and the common line path is opened, the common line path staying open toward a breathing air source of the exhaled air or an ambient air source, and a pumping capacity generated in the common line path by a pressure of the calibrating gas being higher than a pumping capacity caused by the feed pump.

Concept 8. The method according to Concept 7 or any other Concept, wherein the calibrating gas is pumped by a pressure at a pumping capacity of about 310 mL/min and the exhaled air or the ambient air is pumped into the common line path at a pumping capacity of about 210 mL/min by being driven by the feed pump.

Concept 9. The method according to Concept 1 or any other Concept, wherein a purging vessel is provided along the common line path, the exhaled air flowing through said purging vessel and liquid droplets being removed from the exhaled air.

Concept 10. The method according to any one of Concept 1 or any other Concept, further comprising, determining, with the gas sensor, a concentration of oxygen in the exhaled air.

Concept 11. The method according to Concept 1 or any other Concept, further comprising, determining, with the gas sensor, a concentration of carbon dioxide in the exhaled air.

Concept 12. A device for breath gas analysis, the device comprising:
a first intake, external to the device, for exhaled air from a subject and for ambient air;
a first line path for the exhaled air and the ambient air, the line path extending from the first intake into the device;
at least one gas sensor disposed within the device along the line path; a second intake, external to the device, for a calibration gas; and
a second line path extending from the second intake to a portion of the first line path, the portion disposed external to the device such that the second intake is fluidly coupled to the at least one gas sensor via the second line path and the first line path.

Concept 13. The device of Concept 12 or any other Concept, further comprising a valve on the second line path between the second intake and the portion of the first line path.

Concept 14. The device of Concept 13 or any other Concept, further comprising a feed pump configured to pump the exhaled air and the ambient air from the first intake to the at least one gas sensor.

Concept 15. The device of Concept 14 or any other Concept, wherein the feed pump is connected downstream of the at least one gas sensor to configured the feed pump to suck the exhaled air and the ambient air is through the at least one gas sensor.

Concept 16. The device of Concept 15 or any other Concept, wherein the at least one gas sensor comprises two gas sensors.

Concept 17. The device of Concept 16 or any other Concept, wherein the two gas sensor comprise an oxygen sensor and a carbon dioxide sensor.

Concept 18. The device of Concept 14 or any other Concept, further comprising a purging vessel on the first line path between the first intake and the at least one gas sensor.

Concept 19. The device of Concept 12 or any other Concept, further comprising a calibration gas container coupled to the second intake and containing compressed calibration gas.

Concept 20. A method, comprising:
providing ambient air along a line path of a gas analysis device to a gas sensor disposed within the device;
providing exhaled air from a subject along the same line path to the gas sensor; and
providing a calibration gas along the same line path to the gas sensor while the line path is open to the ambient air or the exhaled air.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed:

1. A method of breath gas analysis, comprising:
   determining, by at least one gas sensor of a device for breath gas analysis, a first gas concentration in ambient air received from a first intake of the device through a first line path between the first intake and the at least one gas sensor;
   determining an ambient air reference value based on the first gas concentration;
   determining, by the at least one gas sensor, a second gas concentration in a calibrating gas received from a second intake of the device through a second line path between the second intake and the first line path, the second line path comprising a valve configured to selectively provide the calibration gas to displace ambient air along the first line path;
   determining a calibrating gas reference value based on the second gas concentration;
   determining, by the at least one gas sensor, a third gas concentration in exhaled air received through the first line path from the first intake;
   determining a measured value based on the third gas concentration;
   determining, by the at least one gas sensor, a fourth gas concentration in additional calibrating gas received through the second line path from the second intake;
   determining a correction value based on a difference between the fourth gas concentration and the calibration gas reference value;
   determining a corrected ambient air reference value based on the correction value;

determining, by the at least one gas sensor, a fifth gas concentration in additional exhaled air received through the first line path from the first intake; and performing a breath gas analysis of the fifth gas concentration using the corrected ambient air reference value.

2. The method according to claim 1, wherein the ambient air, the calibrating gas and the exhaled air are fed to the at least one sensor via the first line path.

3. The method according to claim 2, wherein, while the calibrating gas is fed into the first line path, said first line path stays open toward an ambient air source, the calibrating gas being pumped into the first line path at a higher pumping capacity than the ambient air, and the ambient air being displaced from the first line path by the calibrating gas because of the difference in pumping capacity.

4. The method according to claim 2, further comprising: pumping the calibrating gas into the first line path from a pressurized gas cylinder.

5. The method according to claim 4, further comprising: flowing the calibrating gas through at least one pressure throttle.

6. The method according to claim 2, further comprising: pumping the exhaled air and the ambient air through the first line path by a feed pump.

7. The method according to claim 6, further comprising: generating a vacuum by the feed pump disposed downstream of the at least one gas sensor to pump the exhaled air and the ambient air through the first line path.

8. The method according to claim 6, further comprising: opening the valve when the calibrating gas is fed into the second line path so the calibrating gas reaches the first line path;

keeping the first line path open toward a breathing air source of the exhaled air or an ambient air source; and generating a pumping capacity in the first line path by a pressure of the calibrating gas being higher than a pumping capacity caused by the feed pump.

9. The method according to claim 6, further comprising: pumping the calibrating gas by a pressure at a pumping capacity of about 310 mL/min; and pumping, by the feed pump, the exhaled air or the ambient air into the first line path at a pumping capacity of about 210 mL/min.

10. The method according to claim 2, further comprising: removing liquid droplets from the exhaled air by flowing the exhaled air through a purging vessel along the first line path.

11. The method according to claim 1, further comprising; determining, with the at least one gas sensor, a concentration of oxygen in the exhaled air.

12. The method according to claim 1, further comprising: determining, with the at least one gas sensor, a concentration of carbon dioxide in the exhaled air.

13. The method according to claim 1, wherein the first intake is disposed external to the device, the first intake configured to receive the exhaled air from a subject and to receive the ambient air from around the first intake.

14. The method according to claim 1, wherein the first line path extends into the device from the first intake that is external to the device.

15. The method according to claim 14, wherein the second intake is disposed external to the device, and wherein the second line path extends into the device from the second intake.

16. The method according to claim 15, wherein the second line path extends out of the device and connects with the first line path external to the device.

17. The method according to claim 15, wherein the second line path connects with the first line path within the device.

18. The method according to claim 15, further comprising:

measuring an oxygen level with a first sensor; and
measuring a carbon dioxide level with a second sensor.

19. A device for performing the breath gas analysis of claim 1, the device comprising:

the first intake disposed external to the device;
the first line path extending from the first intake into the device;
the at least one gas sensor disposed within the device along the first line path;
the second intake disposed external to the device;
the second line path extending from the second intake into a first portion of the device;
the valve disposed within the device along the second line path; and
the second line path extending out of a second portion of the device and terminating into the first line path external to the device.

20. A device for performing the breath gas analysis of claim 1, the device comprising:

the first intake disposed external to the device;
the first line path extending from the first intake into the device;
the at least one gas sensor disposed within the device along the first line path;
the second intake disposed external to the device;
the second line path extending from the second intake into the device and terminating into the first line path within the device; and
the valve disposed within the device along the second line path.

* * * * *